United States Patent
Tokida

(10) Patent No.: US 11,406,356 B2
(45) Date of Patent: Aug. 9, 2022

(54) IMAGE DIAGNOSIS CATHETER

(71) Applicant: TERUMO KABUSHIKI KAISHA, Tokyo (JP)

(72) Inventor: Masanori Tokida, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 464 days.

(21) Appl. No.: 16/371,407

(22) Filed: Apr. 1, 2019

(65) Prior Publication Data

US 2019/0298308 A1 Oct. 3, 2019

(30) Foreign Application Priority Data

Mar. 30, 2018 (JP) .............................. JP2018-068337

(51) Int. Cl.
| | |
|---|---|
| *A61B 8/00* | (2006.01) |
| *A61B 5/00* | (2006.01) |
| *A61B 8/12* | (2006.01) |
| *A61B 8/08* | (2006.01) |

(52) U.S. Cl.
CPC .......... *A61B 8/4416* (2013.01); *A61B 5/0066* (2013.01); *A61B 5/0084* (2013.01); *A61B 5/6852* (2013.01); *A61B 8/0891* (2013.01); *A61B 8/12* (2013.01); *A61B 8/445* (2013.01); *A61B 8/4461* (2013.01); *A61B 2562/0204* (2013.01); *A61B 2562/0233* (2013.01)

(58) Field of Classification Search
CPC ... A61B 8/4416; A61B 8/4461; A61B 5/6852; A61B 5/0084; A61B 8/0891; A61B 5/0066; A61B 8/12; A61B 8/445; A61B 2562/0204; A61B 2562/0233
See application file for complete search history.

(56) References Cited

U.S. PATENT DOCUMENTS

| | | | |
|---|---|---|---|
| 8,808,186 B2 * | 8/2014 | Fruland | A61B 8/12 600/459 |
| 2012/0123352 A1 | 5/2012 | Fruland et al. | |
| 2017/0079617 A1 | 3/2017 | Yamamoto | |
| 2017/0181728 A1 | 6/2017 | Tokida | |

FOREIGN PATENT DOCUMENTS

JP  2015164660 A  9/2015

OTHER PUBLICATIONS

European Office Action dated Aug. 6, 2020 issued by the European Patent Office in corresponding European Patent Application No. 19166100.8 (6 pages).

* cited by examiner

*Primary Examiner* — Joel Lamprecht

(74) *Attorney, Agent, or Firm* — Buchanan Ingersoll & Rooney PC

(57) ABSTRACT

An image diagnosis catheter that is configured to inhibit separation of a reflective coating of an optical transceiver includes an elongated sheath having a lumen, a rotatable drive shaft disposed in the lumen of the sheath, a housing disposed at the distal end portion of the drive shaft, and an optical transceiver held in the housing. The optical transceiver has a flat surface coated with a reflective coat, which reflects light propagating in an axial direction of the drive shaft. The housing has two side wall portions disposed to interpose at least the reflecting surface of the optical transceiver therebetween.

22 Claims, 9 Drawing Sheets

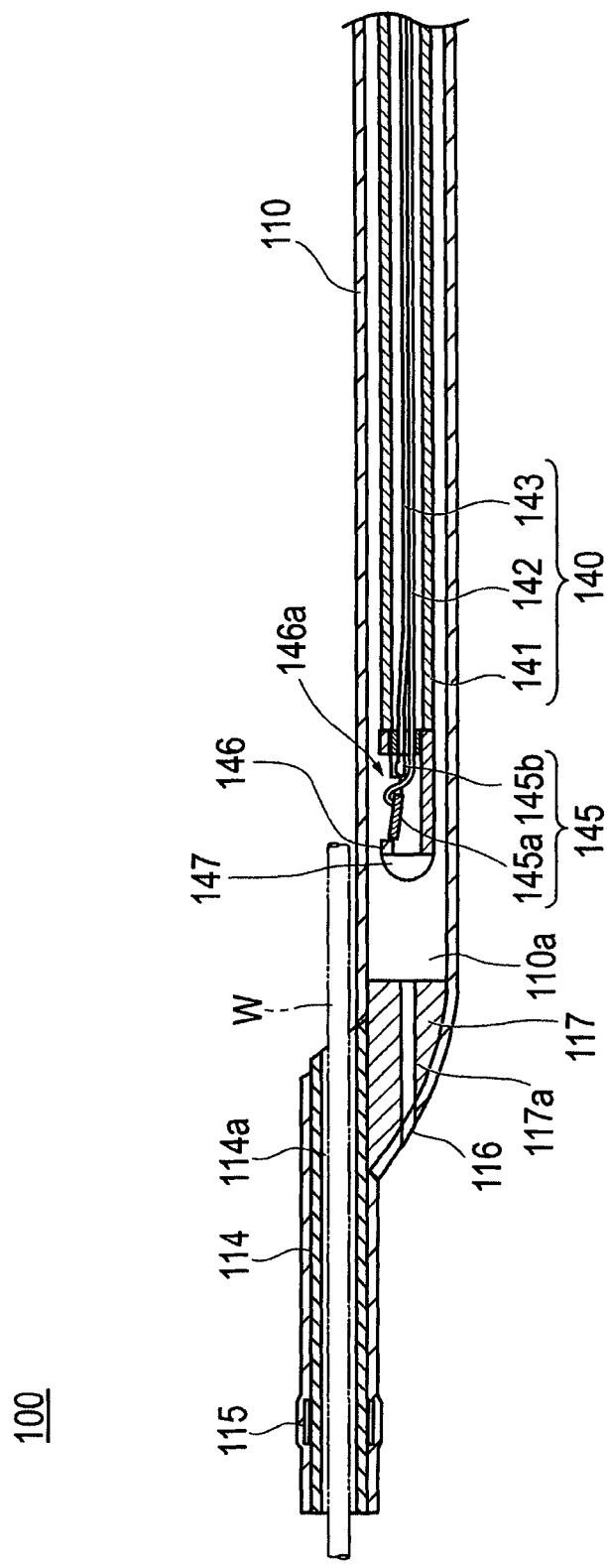

IMAGE DIAGNOSIS CATHETER

CROSS-REFERENCES TO RELATED APPLICATIONS

This application claims priority under 35 U.S.C. § 119(a) to Japanese Application No. 2018-068337 filed on Mar. 30, 2018, the entire content of which is incorporated herein by reference.

FIELD OF THE INVENTION

The present invention generally relates to an image diagnosis catheter.

BACKGROUND DISCUSSION

In recent years, progress has been made developing a dual-type image diagnosis catheter as a medical apparatus to be used for acquiring diagnostic images for diagnosis of disease portions or the like in a living body. An example is disclosed in Japanese Patent Application Publication No. 2015-164660. The dual-type image diagnosis catheter functions to perform both an intravascular ultrasound (IVUS) diagnostic technique and an optical coherence tomography (OCT) diagnostic technique.

The dual-type image diagnosis catheter described in Japanese Patent Application Publication No. 2015-164660 includes a rotatable torque cable including an ultrasound transceiver and an optical transceiver provided at a distal end and a sheath having a lumen in which the torque cable is rotatably inserted. In order to acquire a tomographic image by the image diagnosis catheter, a so-called pull-back operation (internal pulling operation) or a pushing operation for pushing a drive shaft toward the distal side are performed. The pull-back operation includes inserting the sheath into a biological lumen, filling the sheath with a priming liquid, and in this state, retracting the torque cable in the sheath while rotating the cable, so that the torque cable is moved from a distal side to a proximal side. Simultaneously with this operation, the ultrasound transceiver transmits an ultrasound wave toward a wall of the biological lumen, and receives a reflected wave reflected from the wall of the biological lumen. Simultaneously, an optical transceiver also transmits light toward the wall of the biological lumen and receives reflected light reflected from the wall of the biological lumen.

SUMMARY

In the dual-type image diagnosis catheter disclosed in Japanese Patent Application Publication No. 2015-164660 described above, the optical transceiver includes a reflecting surface configured to reflect light propagating through the torque cable, and the optical transceiver is disposed at a position spaced from a center of rotation in a radial direction. In order to arrange both of the ultrasound transceiver and the optical transceiver in a limited space in the sheath, the optical transceiver may be obliged to be located spaced from the center of rotation in the radial direction in this manner.

However, according to the investigation by the inventers, in a case where a reflective coating, which can reflect light, is applied on the reflecting surface, the farther the optical transceiver is arranged from the center of rotation in the radial direction, the more likely that the reflective coating on the reflecting surface is separated due to a flow of the priming liquid during the rotation, so that an accurate tomographic image may not be acquired.

The image diagnosis catheter disclosed here is configured to inhibit separation of a reflective coating of an optical transceiver.

To achieve the above object, the present invention is directed to an image diagnosis catheter for acquiring a tomographic image of a biological lumen, the image diagnosis catheter including: an elongated sheath having a lumen; a rotatable elongated member disposed in the lumen of the sheath; a housing disposed at a distal end portion of the elongated member; and an optical transceiver held in the housing, in which the optical transceiver has a reflecting surface provided with a reflective coat that reflects light propagating in an axial direction of the elongated member, and the housing has two side wall portions disposed to interpose at least the reflecting surface of the optical transceiver therebetween.

The image diagnosis catheter of the present invention can inhibit or prevent separation of the reflective coat, which would otherwise be caused by the two side wall portions covering the reflecting surface.

BRIEF DESCRIPTION OF THE DRAWINGS

FIG. 3 is a cross-sectional view illustrating a distal end portion of the image diagnosis catheter according to the embodiment of the present invention.

DETAILED DESCRIPTION

Set forth below with reference to the accompanying drawings is a detailed description of embodiments of an image diagnosis catheter and operation method representing examples of the inventive image diagnosis catheter and operation method disclosed here. The dimensions or scales on the drawings may be exaggerated or different from actuality/reality for convenience of description and illustration. The following description is not intended to limit the technical scope or significance of terms described in Claims.

Figure 1:
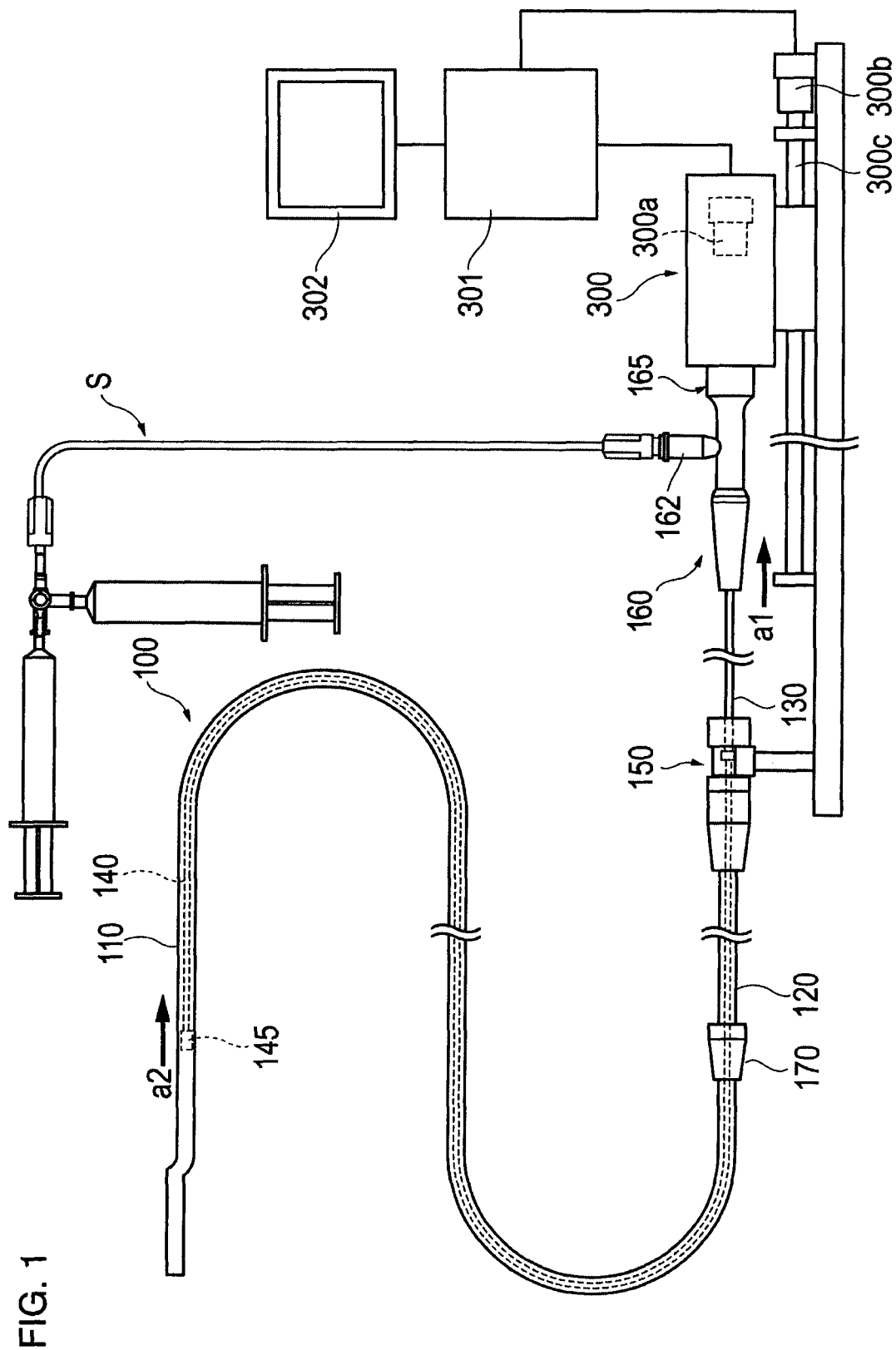
FIG. 1 is a drawing illustrating a state in which an eternal device is connected to an image diagnosis catheter according to an embodiment of the present invention.
Figure 2A:
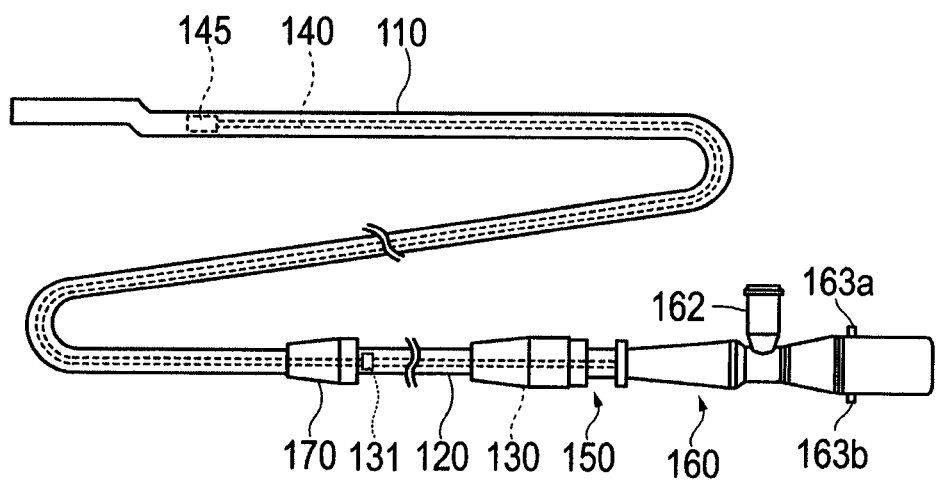
FIG. 2A is a side view illustrating a state before performing a pull-back operation (internal pulling operation) of the image diagnosis catheter according to the embodiment of the present invention.
Figure 2B:
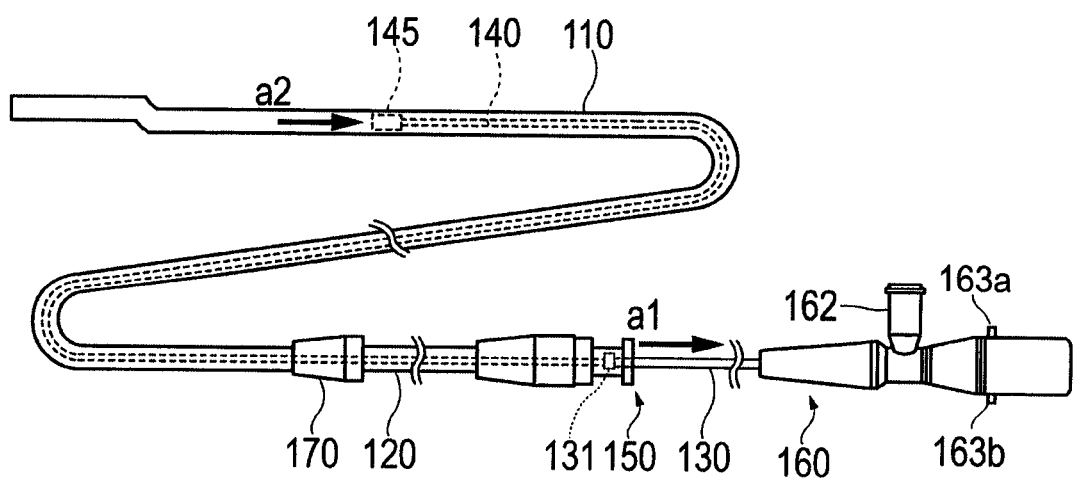
FIG. 2B is a side view illustrating the pull-back operation of the image diagnosis catheter according to the embodiment of the present invention.

FIG. 1 to FIG. 2B illustrate the entire configuration of an image diagnosis catheter 100 according to an embodiment representing an example of the image diagnosis catheter disclosed here. FIG. 3 to FIG. 8 are drawings for explaining individual parts of the image diagnosis catheter 100. FIG. 9A and FIG. 9B are cross-sectional views schematically illustrating a usage example of the image diagnosis catheter 100.

The image diagnosis catheter 100 is a dual-type image diagnosis catheter having functions to perform both an intravascular ultrasound (IVUS) diagnosis technique and an optical coherence tomography (OCT) diagnosis technique. The dual-type image diagnosis catheter 100 includes three modes, that is, a mode for acquiring a tomographic image only with the IVUS, a mode for acquiring a tomographic image only with the OCT, and a mode for acquiring a tomographic image with the IVUS and the OCT, and may be used by switching the mode among these modes. As illustrated in FIG. 1, the image diagnosis catheter 100 is driven by being connected to an external device 300.

Referring to FIG. 1 to FIG. 4, the image diagnosis catheter 100 will be described.

As illustrated in FIG. 1, FIG. 2A, and FIG. 2B, the image diagnosis catheter 100 includes, generally speaking, a sheath 110 to be inserted into a lumen in a living body, an outer tube 120 provided on a proximal side of the sheath 110, an inner shaft 130 to be inserted into the outer tube 120 so as to be movable forward and backward, a drive shaft 140 (corresponds to "elongated member") including a signal transceiver 145 configured to transmit and receive a signal at a distal end and provided rotatably in the sheath 110, a unit connector 150 provided on a proximal side of the outer tube 120 and configured to receive the inner shaft 130, and a hub 160 provided on a proximal side of the inner shaft 130.

In the following description, a side of the image diagnosis catheter 100 inserted into a lumen in a living body is referred to as the "distal side" or "distal end" and a side of the hub 160 provided on the image diagnosis catheter 100 is referred to as the "proximal side" or "proximal end". An extending direction of the sheath 110 is referred to as the "axial direction". Regarding the image diagnosis catheter 100 and the individual components, a portion including a certain range from a distal end (distal-most end) in the axial direction is defined as "distal end portion", and a portion including a certain range from a proximal end (proximal-most end) in the axial direction is defined as "proximal portion".

As illustrated in FIG. 2A, the drive shaft 140 passes through the sheath 110, the outer tube 120 connected to the proximal end of the sheath 110, and the inner shaft 130 to be inserted into the outer tube 120, and extends up to an interior of the hub 160.

The hub 160, the inner shaft 130, the drive shaft 140, and the signal transceiver 145 are connected to each other and move integrally forward and backward in the axial direction. Therefore, when an operation that the hub 160 is pressed or moved toward the distal side (distal direction), for example, is performed, the inner shaft 130 connected to the hub 160 is pushed or moved inside the outer tube 120 and inside the unit connector 150, and the drive shaft 140 and the signal transceiver 145 are moved inside the sheath 110 to the distal side or in the distal direction. For example, when an operation is performed in which the hub 160 is pulled to the proximal side or in the proximal direction, the inner shaft 130 is pulled from the outer tube 120 and the unit connector 150 as indicated by arrows a1 in FIG. 1 and FIG. 2B, and the drive shaft 140 and the signal transceiver 145 move in the sheath 110 toward the proximal end as indicated by arrows a2.

As illustrated in FIG. 2A, when the inner shaft 130 is pushed in toward the distal side or in the distal direction to the maximum extent, the distal end portion of the inner shaft 130 reaches a position near a relay connector 170. At this time, the signal transceiver 145 is located near a distal end of the sheath 110. The relay connector 170 is a connector configured to connect the sheath 110 and the outer tube 120.

As illustrated in FIG. 2B, a retaining connector 131 is provided at a distal end of the inner shaft 130. The retaining connector 131 functions to prevent the inner shaft 130 from slipping out from the outer tube 120. The retaining connector 131 is configured to be caught at a predetermined position on an inner wall of the unit connector 150 when the hub 160 is pulled to the proximal side or in the proximal direction to the maximum extent, that is, when the inner shaft 130 is pulled out from the outer tube 120 and the unit connector 150 to the maximum.

As illustrated in FIG. 3, the drive shaft 140 includes a tubular body 141 having flexibility, and an electric signal cable 142 and an optical fiber 143, which are to be connected to the signal transceiver 145, are disposed in the interior of the tubular body 141. The tubular body 141 may be fabricated from a multi-layer coil composed of layers wound around an axis in different directions. Examples of the material of the coil include stainless steel, and Ti—Ni (nickel-titanium) alloy. The electric signal cable 142 in this embodiment includes two signal lines 142a and 142b (see FIG. 5) electrically connected to an electrode terminal 165a (see FIG. 4) provided on a connector unit 165, which will be described later.

The signal transceiver 145 includes an ultrasound transceiver 145a configured to transmit and receive ultrasound, and an optical transceiver 145b configured to transmit and receive light.

The ultrasound transceiver 145a includes an oscillator and functions to transmit ultrasound based on the pulse signal into a lumen in a living body, and receive the ultrasound reflected from a biological tissue in the lumen in the living body. The ultrasound transceiver 145a is electrically connected to the electrode terminal 165a (see FIG. 4) via the electric signal cable 142.

Examples of the oscillator provided on the ultrasound transceiver 145a include piezoelectric material such as ceramics and crystal.

The optical transceiver 145b transmits transferred light continuously into the lumen in the living body, and continuously receives the light reflected from the biological tissue in the lumen in the living body. The optical transceiver 145b includes an optical element at a distal end of the optical fiber 143. The optical element has a lens function to concentrate light and a reflecting function to reflect light.

Figure 7:
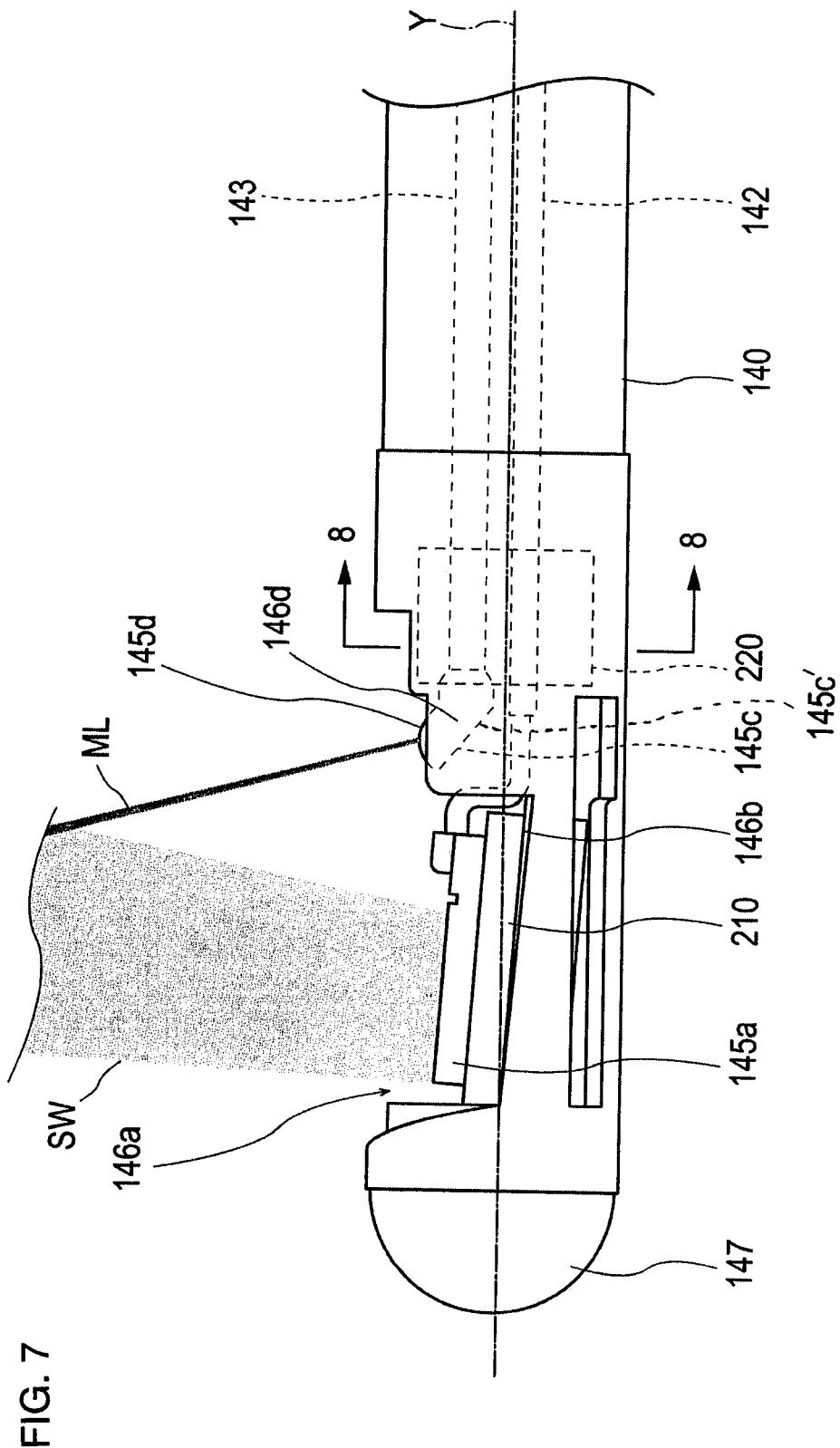
FIG. 7 is a side view of FIG. 5.

The optical element provided on the optical transceiver 145b in this embodiment includes a ball lens having a flat surface 145c and a spherical surface 145d, as illustrated in FIG. 7. The flat surface 145c is coated with a reflective coating (schematically identified as 145c' in FIG. 7) for reflecting light propagating from the optical fiber 143. Examples of the material of the reflective coat include aluminum, although it is not specifically limited to such material as long as light can be reflected. Light propagating from the optical fiber 143 is reflected on the flat surface 145c, is concentrated on the spherical surface 145d, and then is transmitted into the lumen in the living body. The light reflected from the biological tissue in the lumen in the living body is concentrated on the spherical surface 145d, is reflected on the flat surface 145c, and then is allowed to propagate into the optical fiber 143. The configuration of the optical transceiver 145b is not specifically limited as long as the reflecting surface coated with a reflective coating for reflecting light propagating from the optical fiber 143 is provided. For example, the optical transceiver 145b may include a plate member provided with the reflective coating.

The signal transceiver 145 is stored or positioned in the interior of a housing 146 as illustrated in FIG. 3. A proximal portion of the housing 146 is connected to the drive shaft 140. The housing 146 is a cylindrical metal pipe or tube and has a shape provided with an opening or opening portion 146a on a cylindrical surface so that advancement of the ultrasound transmitted and received by the ultrasound transceiver 145a and light transmitted and received by the optical transceiver 145b is not obstructed. The opening in the housing 146 passes through the wall that surrounds the interior of the housing 146 so that the opening portion 146a opens to the interior of the housing 146 and communicates the interior of the housing 146 with the exterior of the housing 146. The housing 146 may be formed, for example, by laser processing. Examples of the method of formation of the housing 146 include filing out a metal block, and metallic powder injection molding (MIM).

A distal end member 147 is provided at a distal end of the housing 146. The distal end member 147 has a substantially semispherical outer shape. By forming the distal end member 147 into the semispherical shape, friction or scratching with an inner surface of the sheath 110 can be reduced. The distal end member 147 may be fabricated, for example, from a coil. The distal end member 147 does not have to be provided at the distal end of the housing 146.

The sheath 110 includes a lumen 110a. In the lumen 110a, the drive shaft 140 is inserted or positioned so that the drive shaft 140 is movable forward and backward. A guide wire insertion member 114 including a guide wire lumen 114a is attached to a distal end portion of the sheath 110. The guide wire lumen 114a is provided in parallel with the lumen 110a provided in sheath 110 and allows insertion of a guide wire W, described later. The sheath 110 and the guide wire insertion member 114 may be formed integrally, for example, by heat welding. The guide wire insertion member 114 is provided with a marker 115 capable of forming an X-ray image. The marker 115 includes a tubular made of a highly radio-opaque metal such as platinum (Pt) or gold (Au). In this regard, Pt (mentioned above) may be mixed with iridium (Ir) to form an alloy for the purpose of improvement of mechanical strength. Furthermore, the marker 115 may be fabricated from a metal coil instead of the metal pipe or tube.

The sheath 110 is provided with a communication hole 116 formed at the distal end portion for communicating an interior and an exterior of the lumen 110a. The sheath 110 is also provided with a reinforcing member 117 at the distal end portion for firmly joining and supporting the guide wire insertion member 114. The reinforcing member 117 includes a communication path 117a configured to communicate an interior of the lumen 110a disposed on the proximal side with respect to the reinforcing member 117 with the communication hole 116. The reinforcing member 117 does not have to be provided at the distal end portion of the sheath 110.

The communication hole 116 is a priming liquid discharge hole for discharging a priming liquid. When the image diagnosis catheter 100 is used, a priming process is performed to fill the sheath 110 with the priming liquid. When ultrasound is sent without filling the sheath 110 with the priming liquid, the ultrasound may be reflected from an interface between a matching layer and the air due to a large difference in an acoustic impedance of the matching layer disposed on the surface of the transducer of the ultrasound transceiver 145a and the air. Consequently, the ultrasound cannot reach deep enough to a wall of a biological lumen. In contrast, by filling the sheath 110 with a priming liquid having an acoustic impedance close to that of the matching layer, the ultrasound can reach deep enough to the wall of the biological lumen. When performing the priming process, the priming liquid is discharged out through the communication hole 116 to expel gas such as air from the interior of the sheath 110 together with the priming liquid.

The distal end portion of the sheath 110, which is a range in which the signal transceiver 145 moves in the axial direction of the sheath 110, constitutes a window part formed with a higher transmittance of an inspection wave such as light and ultrasound than other parts.

Materials of the sheath 110, the guide wire insertion member 114, and the reinforcing member 117 preferably have flexibility, but are not specifically limited. Examples of the materials include thermoplastic elastomers of styrene-based, polyolefin-based, polyurethane-based, polyester-based, polyimide-based, polyimide-based, polybutadiene-based, trans polyisoprene-based, fluoro-rubber-based, and chlorinated polyethylene-based, and also include a combination of one or two or more of these (polymer alloy, polymer blend, laminated products, etc.). A hydrophilic lubricating coating layer that exhibits lubricity when wetting may be disposed on an outer surface of the sheath 110.

Figure 4:
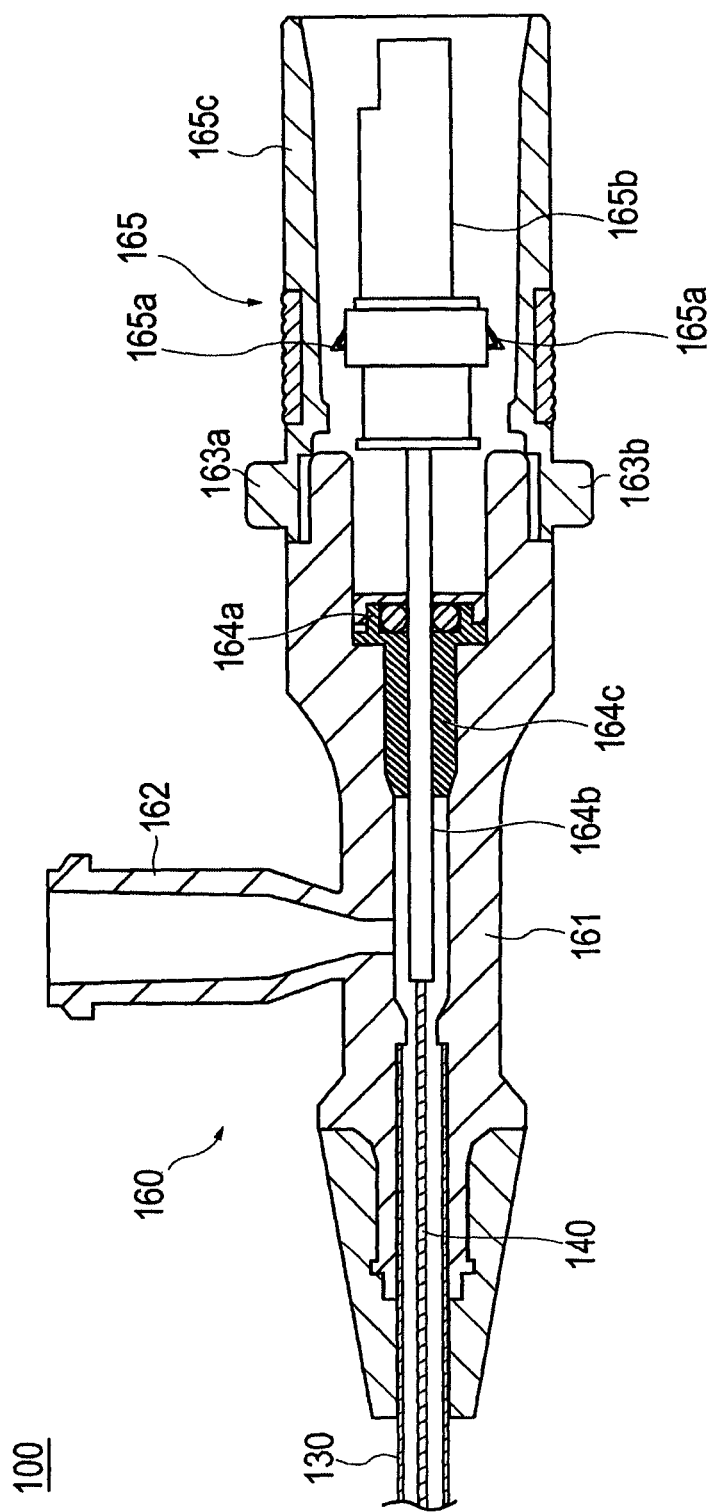
FIG. 4 is a cross-sectional view illustrating a proximal portion of the image diagnosis catheter according to the embodiment of the present invention.

As illustrated in FIG. 4, the hub 160 includes a hub body 161 having a hollow shape, a connector case 165c connected to a proximal side of the hub body 161, a port 162 communicating with an interior of the hub body 161, protrusions 163a and 163b configured to fix the position (direction) of the hub 160 for connecting the external device 300 to the hub 160, a connecting pipe or tube 164b configured to retain the drive shaft 140, a bearing 164c configured to rotatably support the connecting pipe or tube 164b, a seal member 164a configured to prevent the priming liquid from leaking from between the connecting tube 164b and the bearing 164c toward the proximal side, and a connector unit 165 including, in the interior thereof, the electrode terminal 165a and an optical connector 165b connected to the external device 300.

The inner shaft 130 is connected to the distal end portion of the hub body 161. The drive shaft 140 is drawn out from or extends outwardly from the inner shaft 130 in the interior of the hub body 161.

An injection device S (see FIG. 1) configured to inject priming liquid is connected to the port 162 when performing the priming process.

The connecting tube 164b holds or is connected to the drive shaft 140 in order to transmit the rotation of the electrode terminal 165a and the optical connector 165b rotated by the external device 300 to the drive shaft 140. The electrical signal cable 142 and the optical fiber 143 (see FIG. 3) are inserted into or positioned in an interior of the connecting tube 164b.

The connector unit 165 is provided with the electrode terminal 165a electrically connected to the electrical signal cable 142 and the optical connector 165b connected to the optical fiber. The received signal of the ultrasound transceiver 145a is transmitted to the external device 300 via the electrode terminal 165a, and is subjected to a predetermined processing to display it as an image. The received signal of the optical transceiver 145*b* is transmitted to the external device 300 via the optical connector 165*b*, and is subjected to a predetermined processing to display it as an image.

Referring again to FIG. 1, the image diagnosis catheter 100 is driven by being connected to the external device 300.

As described above, the external device 300 is connected to the connector unit 165 provided on the proximal side of the hub 160.

The external device 300 includes a motor 300*a*, which is a power source for rotating the drive shaft 140, and a motor 300*b*, which is a power source for moving the drive shaft 140 in an axial direction. The rotational motion of the motor 300*b* is converted into an axial motion by a direct motion conversion mechanism 300*c* connected to the motor 300*b*. As the direct motion conversion mechanism 300*c*, for example, a ball screw, a rack and pinion mechanism, or the like may be used.

The operation of the external device 300 is controlled by a controller 301, which is electrically connected to the external device 300. The controller 301 includes a Central Processing Unit (CPU) and a memory as main configurations. The controller 301 is electrically connected to a monitor 302.

Next, referring to FIG. 5 to FIG. 8, the housing 146, the ultrasound transceiver 145*a*, the optical transceiver 145*b*, and the like will be described in detail. In the following description, the side of the housing 146 where the opening 146*a* is provided (upper side of FIG. 7) is referred to as an upper side. A rotating shaft of the drive shaft 140 is referred to as a rotation shaft Y. A direction orthogonal to the rotation shaft Y is referred to as the radial direction.

Figure 5:
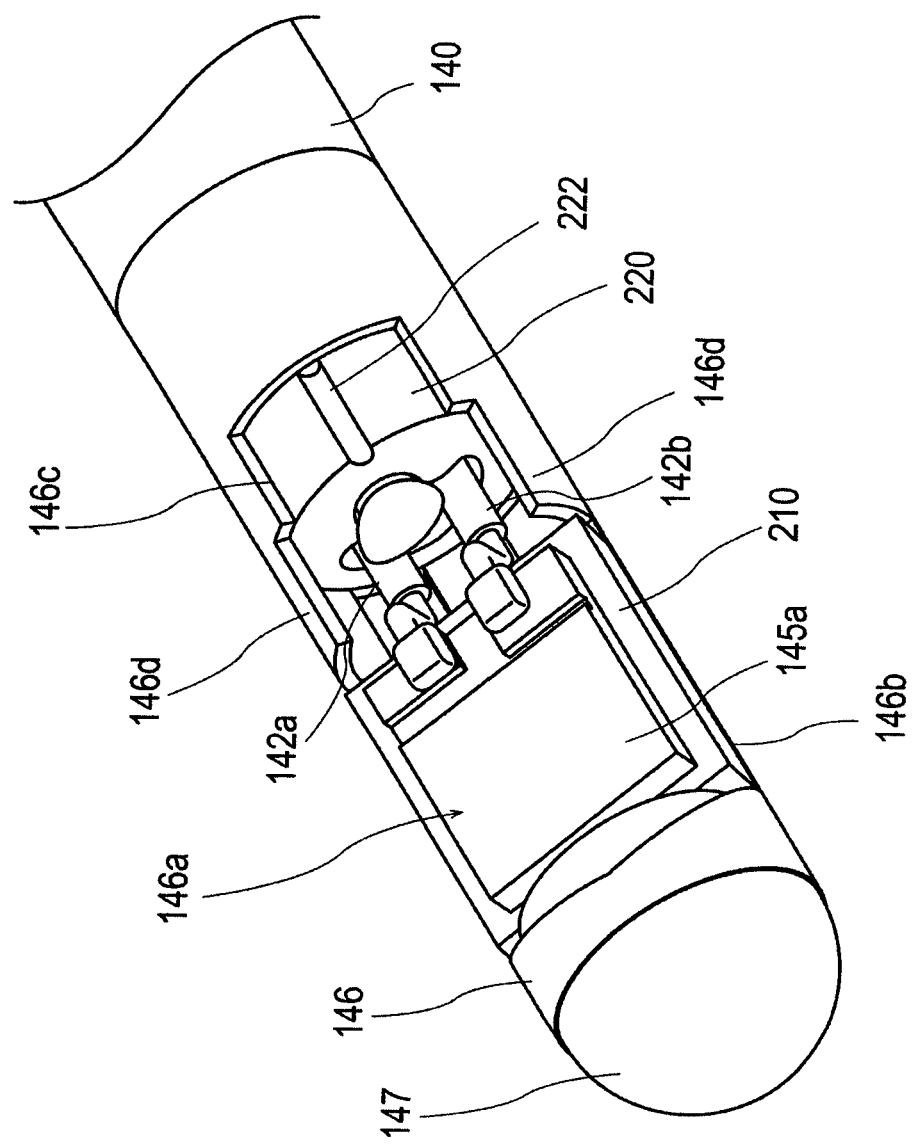
FIG. 5 is a perspective view illustrating a housing, an ultrasound transceiver, and an optical transceiver of the image diagnosis catheter according to the embodiment of the present invention in detail.

As illustrated in FIG. 5 and FIG. 7, the ultrasound transceiver 145*a* is attached to a backing member 210. The backing member 210 scatters and attenuates ultrasound from the ultrasound transceiver 145*a* advancing toward the opposite direction of the opening portion 146*a* of the housing 146. The backing member 210 is attached to an edge 146*b* surrounding the opening portion 146*a* of the housing 146. The method of securing the backing member 210 to the housing 146 is not particularly limited, but it may be secured by adhesion with an adhesive agent, for example. In this embodiment, as illustrated in FIG. 7, the backing member 210 is secured to the housing 146 so that the ultrasound transceiver 145*a* transmits ultrasound SW in a direction inclined toward the proximal side with respect to the radial direction of the drive shaft 140.

The optical transceiver 145*b* is secured to the housing 146 via a positioning member 220 as illustrated in FIG. 5.

In this embodiment, as illustrated in FIG. 7, the positioning member 220 secures the position of the optical transceiver 145*b* so that the ultrasound SW transmitted from the ultrasound transceiver 145*a* and light ML transmitted from the optical transceiver 145*b* intersect each other.

Figure 8:
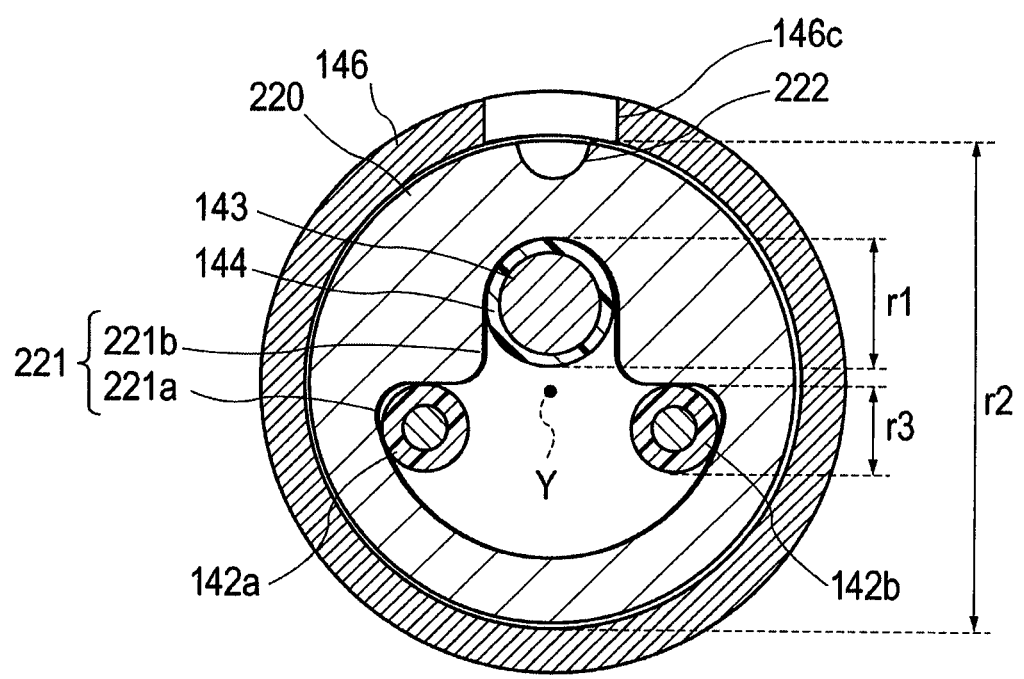
FIG. 8 is a cross-sectional view taken along the section line 8-8 in FIG. 7.
Figure 9A:
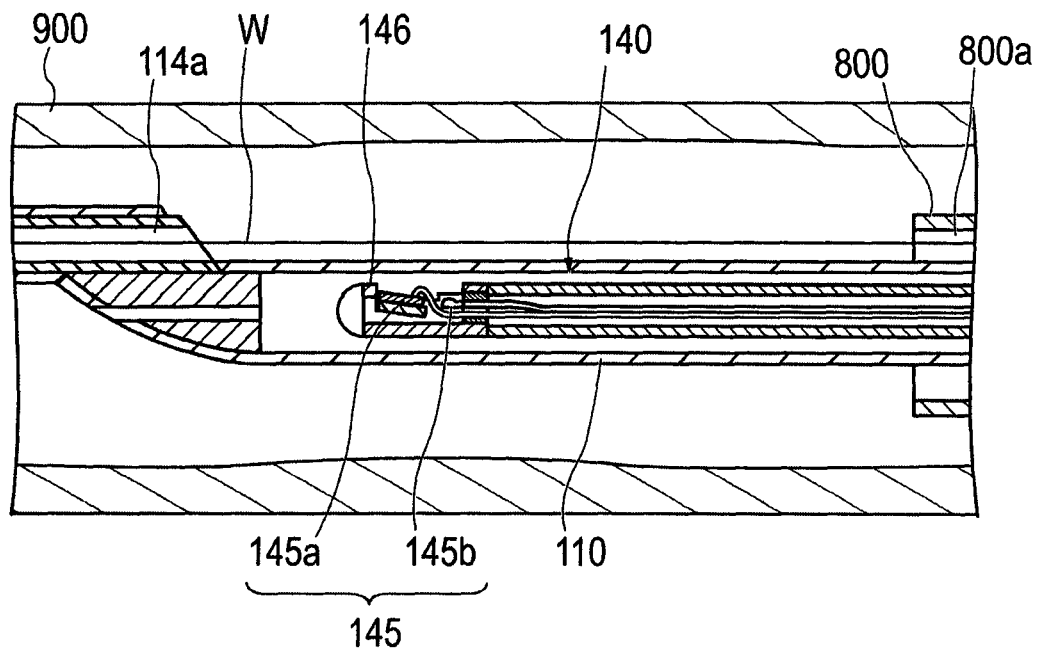
FIG. 9A is a schematic drawing illustrating a usage example of the image diagnosis catheter according to the embodiment of the present invention.
Figure 9B:
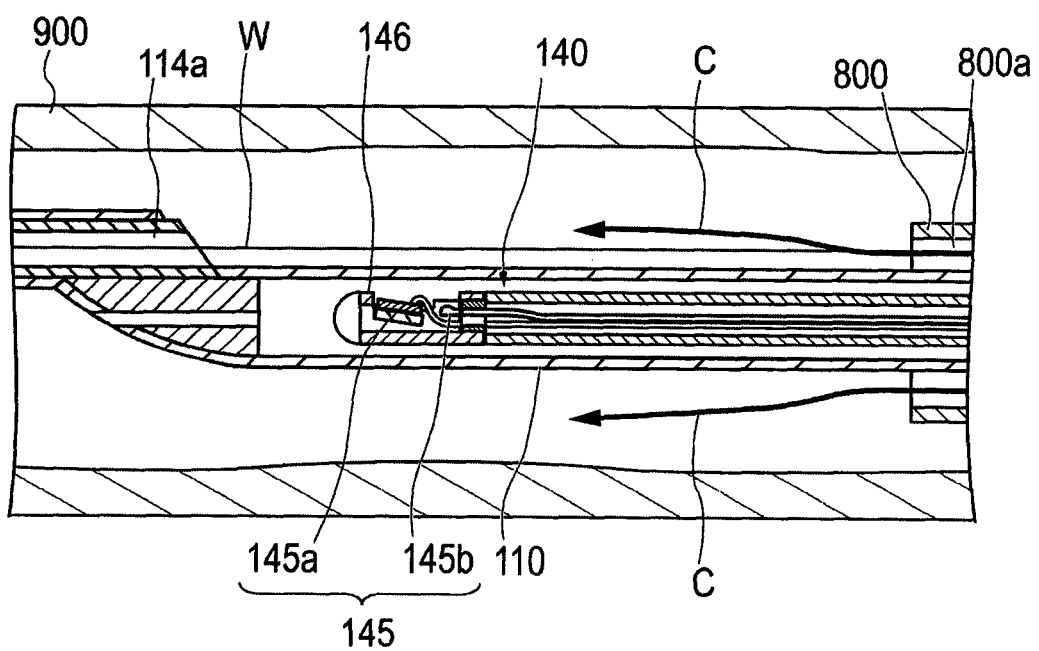
FIG. 9B is a schematic drawing illustrating a usage example of the image diagnosis catheter according to the embodiment of the present invention.

As illustrated in FIG. 7 and FIG. 8, the positioning member 220 has a substantially cylindrical outer shape.

The positioning member 220 is provided with an insertion hole 221 at a substantially center of the positioning member 220. The electric signal cable 142 and the optical fiber 143 may be inserted through or positioned in the insertion hole 221 as illustrated in FIG. 8. The insertion hole 221 includes a first insertion hole part 221*a* formed by cutting the positioning member 220 into a substantially semi-cylindrical shape (as seen in the FIG. 8 transverse cross-section), and a second insertion hole part 221*b* continuing from (i.e., communicating with or opening into) the first insertion hole part 221*a* and allows the optical fiber 143 to be fitted. To protect the interlock portion between the optical fiber 143 and the optical transceiver 145*b*, the interlock portion may be covered with a protective cover 144.

In order to arrange the signal transceiver 145, the electric signal cable 142, the optical fiber 143, the positioning member 220, and the like in the housing 146, the housing 146 having a larger inner diameter r2 is preferable (see FIG. 8). In contrast, an outer diameter of the housing 146 is preferably large enough to desirably maintain the slidability of the sheath 110 in the biological lumen, and needs to have a certain thickness sufficient to ensure the appropriate strength. Therefore, there is a limitation on increasing the inner diameter r2 of the housing 146. There is thus also a limitation on increasing the outer diameter of the positioning member 220 accommodated in the housing 146.

If the optical fiber 143 is disposed so that the axial center of the optical fiber 143 covered with the protective cover 144 is located on (i.e., coaxial with) the rotation axis Y of the drive shaft 140, it becomes difficult to ensure a space (the first insertion hole part 221*a*) for arranging the electric signal cable 142 (two signal lines 142*a*, 142*b*) having a fixed outer diameter r3 due to the outer diameter r1 of the optical fiber 143 including the protective cover 144. Therefore, the positioning member 220 is configured so that the second insertion hole part 221*b* is provided in the positioning member 220 so that the center position of the optical fiber 143 (central axis of the optical fiber 143) which is disposed in the second insertion hole part 221*b* is away from or spaced from the center position (rotational axis Y) of the drive shaft 140. That is, the central axis of the optical fiber 143 is spaced from a plane passing through the central axis of each of the two electric signal cables 142*a*, 142*b*. Accordingly, the space (the first insertion hole part 221*a*) for disposing or accommodating the electric signal cable 142 (signal lines 142*a*, 142*b*) may be secured. Therefore, a center position (center) of the optical transceiver 145*b* is disposed at a position apart from or spaced from the central position (rotation axis Y) of the drive shaft 140 on a cross section orthogonal to the rotation axis Y of the drive shaft 140.

The outer peripheral surface of the positioning member 220 includes an axially extending depression, recess or groove 222 as illustrated in FIG. 8. The depression 222, which will be described in detail later, is used for adjusting the position of the positioning member 220 in a circumferential direction in a stage of manufacture.

The material of the positioning member 220 preferably includes, but is not limited to, a material capable of forming an image under X-ray illumination (a radio-opaque material), such as Pt, Au, or Pt—Ir alloy. By fabricating the positioning member 220 from these materials, a surgeon can easily know the position of the optical transceiver 145*b* under fluoroscopy.

As illustrated in FIG. 7, the positioning member 220 is secured to an inner surface of the housing 146 such that the flat surface 145*c* of the optical transceiver 145*b* is disposed radially inward of the spherical surface 145*d*. The spherical surface 145*d* of the optical transceiver 145*b* faces radially outwardly and the flat surface 145*c* of the optical transceiver 145*b* faces radially inwardly.

As illustrated in FIG. 7, the housing 146 includes a side wall portion 146*d* disposed so as to cover at least the flat reflecting surface 145*c* of the optical transceiver 145*b*. That is, the side wall portion 146*d* disposed so as to cover at least the flat surface 145*c* of the optical transceiver 145*b*. As illustrated in FIG. 5, two of the side wall portions 146*d* are provided so that the optical transceiver 145*b* is transposed between the two side wall portions 146*d* in the circumferential direction. The side wall portions 146d thus cover the flat surface 145c of the optical transceiver 145b in the sense that they cover the flat surface 145c from the sides. The side wall portion 146d is formed integrally in one piece with the housing 146 in this embodiment. However, the side wall portion 146d may be formed separately from the housing 146, and may be joined to the housing 146 by an adhesive agent or the like.

Figure 6:
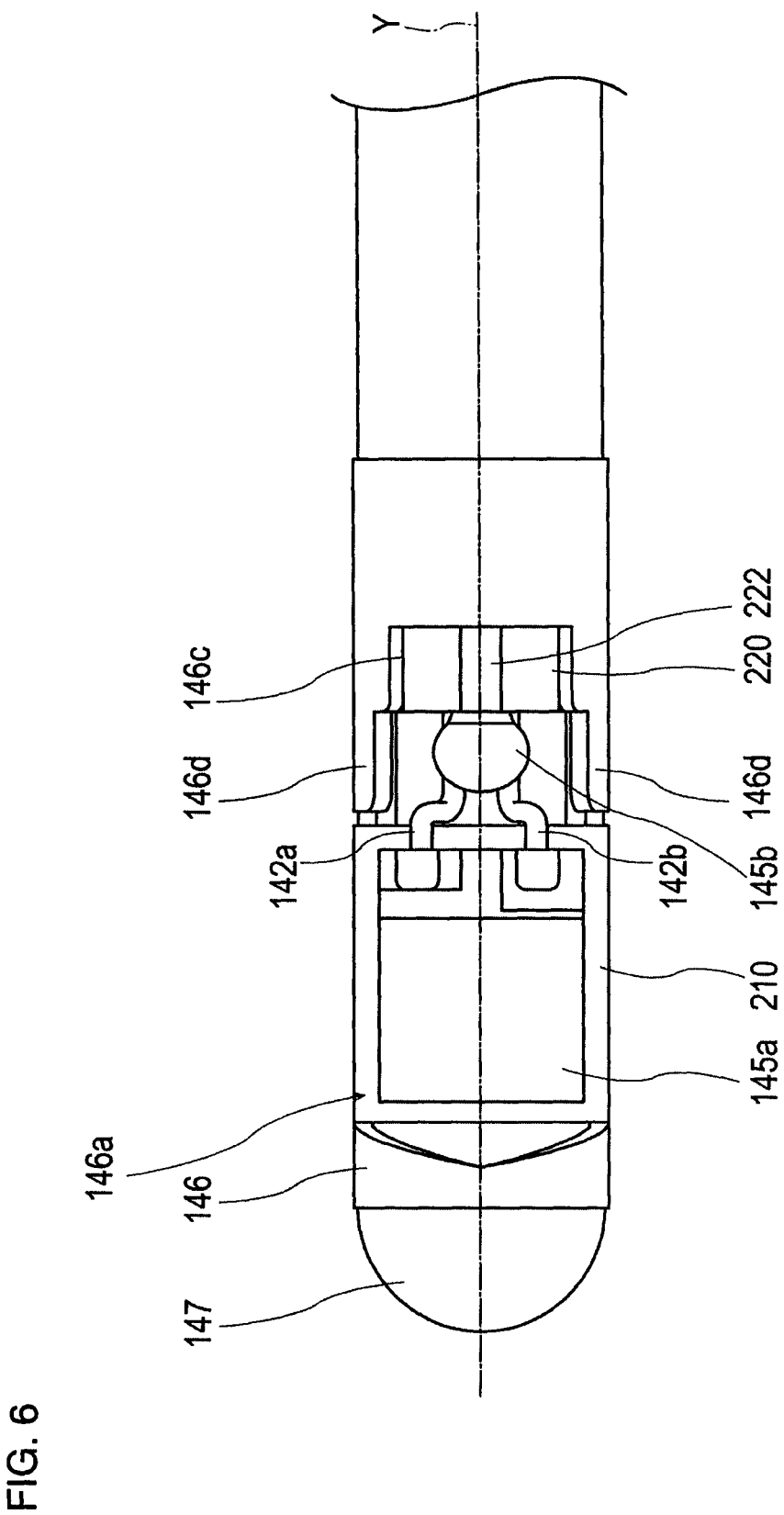
FIG. 6 is a top view of FIG. 5.

As illustrated in FIG. 6 and FIG. 7, the side wall portion 146d is configured to expose the spherical surface 145d (the transmission and reception surface of light) of the optical transceiver 145b while covering the flat surface 145c (i.e., covering the flat surface 145c from the side). Therefore, the side wall portion 146d may be prevented from obstructing the path of light (optical path) transmitted and received by the optical transceiver 145b.

FIG. 5 illustrates that the opening in the housing 146 includes the portion 146a around the ultrasound transceiver 145a (i.e., the portion 146a of the opening at which the ultrasound transceiver 145a is exposed) and the portion around the optical transceiver 145b (i.e., the portion of the opening at which the ultrasound transceiver 145b is exposed). The portion around the optical transceiver 145b is bounded by the side wall portion 146d. FIG. 5 illustrates that the opening opens larger around the ultrasound transceiver 145a than around the optical transceiver 145b. For example, the circumferential extent of the portion of the opening around the ultrasound transceiver 145a is larger than the circumferential extent of the portion of the opening around the optical transceiver 145b.

As illustrated in FIG. 6, the housing 146 includes a notch 146c (axially extending notch) penetrating through a portion where the positioning member 220 is accommodated in a thickness direction. The depression 222 provided on the positioning member 220 and the notch 146c provided on the housing 146 are provided at positions overlapping each other in the radial direction as illustrated in FIG. 8. That is, the positioning member 222 is exposed at the notch 146c. Therefore, for example, at the time of manufacture of the image diagnosis catheter 100, a jig such as a needle or forceps is inserted through the notch 146c to catch the depression 222, and the positioning member 220 is rotated with respect to the housing 146, the position of the positioning member 220 in the circumferential direction with respect to the housing 146 is fine adjusted so that the ultrasound SW and the light ML intersect, and then the positioning member 220 can be secured to the housing 146. The method of securing the positioning member 220 to the housing 146 is not particularly limited, but it may be bonded with an adhesive, for example. In this case, for example, the positioning member 220 can be secured to the housing 146 by rotating the positioning member 220 while an adhesive is injected from the notch 146c and distributed over the peripheral surface of the positioning member 220.

FIG. 9A and FIG. 9B explain an example of use of the image diagnosis catheter 100 according to the embodiment. The following description describes an example of the use of the image diagnosis catheter 100 in a blood vessel 900 (biological lumen).

First, a user connects an injection device S for injecting the priming liquid to the port 162 with the hub 160 pulled to the proximal side or min the proximal direction to the maximum extent, and injects the priming liquid into the lumen 110a of the sheath 110.

When the priming liquid is injected into the lumen 110a, the priming liquid is discharged out from the sheath 110 through the communication path 117a and the is expelled out from the interior of the sheath 110 together with the priming liquid (priming process).

After the priming process, the user connects the external device 300 to the connector unit 165 of the image diagnosis catheter 100, as illustrated in FIG. 1. Then, the user pushes the hub 160 until it attaches or connects to the proximal end of the unit connector 150 (see FIG. 2A) and moves the signal transceiver 145 to the distal side or in the distal direction.

The user then uses an introducer kit (not illustrated) to create a port to introduce the image diagnosis catheter 100 into the biological lumen through a wrist or thigh of the patient. A first guidewire is then inserted through the port into the vicinity of an inlet of the heart's coronary artery. A guiding catheter 800 is then introduced over the first guide wire to the inlet of the coronary artery. Next, the first guidewire is removed and the second guidewire W is inserted through the guiding catheter 800 into a lesion area. Next, the image diagnosis catheter 100 is inserted and moved along the second guidewire W to the lesion area.

Next, as illustrated in FIG. 9A, the image diagnosis catheter 100 is advanced along a lumen 800a to a position protruding distally beyond a distal end opening of the guiding catheter 800. Thereafter, the image diagnosis catheter 100 is further pushed along the second guidewire W while the second guidewire W is inserted through the guidewire lumen 114a, and then is inserted to a target position in the blood vessel 900. Examples of the guiding catheter 800 include a known guiding catheter in which a port (not illustrated) that can connect a syringe (not shown) is provided at a proximal portion.

The blood in the blood vessel 900 is then temporarily replaced with a flush solution, such as a contrast agent. In the same manner as the aforementioned priming process, a syringe containing flush solution is connected to the port of the guiding catheter 800, and the plunger of the syringe is pushed to inject the flush solution into the interior of the lumen 800a of the guiding catheter 800. The flush solution is introduced through the lumen 800a of the guiding catheter 800 into the blood vessel 900 via the distal end opening, as indicated by an arrow C in FIG. 9B. The introduced flush solution pushes the blood around the distal end portion of sheath 110 into a state in which the region around the periphery of the distal end portion of the sheath 110 is filled with the flush solution.

When the tomographic image is acquired at the desired position in the blood vessel 900, the signal transceiver 145 moves toward the proximal side or proximal direction while rotating with the drive shaft 140 (pull back operation). At the same time as the pull-back operation, the ultrasound transceiver 145a transmits the ultrasound SW to a vessel wall 900b and receives ultrasound reflected by or from the vessel wall 900b. Also, the optical transceiver 145b simultaneously transmits the light ML toward the vessel wall 900b, and receives reflected light reflected from the vessel wall 900b.

At this time, the sheath 110 is filled with the priming liquid. According to the investigation by the present inventors, when the flat surface 145c of the optical transceiver 145b is exposed, the reflective coating applied to the flat surface 145c is more likely separated by the flow of the priming liquid at the time of rotation as the distance of the optical transceiver 145b from the rotation axis Y of the drive shaft 140 increases in the radial direction. This seems to be due to the fact that the rotation speed of the optical transceiver 145b becomes faster as the distance of the optical transceiver 145b from the rotation axis Y of the drive shaft 140 increases in the radial direction, and thus, and the resistance received from the priming liquid is increased. In the image diagnosis catheter 100 according to the present embodiment disclosed as an example of the inventive image diagnosis catheter 100 disclosed here, the side wall portion 146d covers the flat surface 145c coated with the reflective coating, which can inhibit or prevent separation of the reflective coating on the flat surface 145c due to the priming liquid at the time of rotation.

The rotation and the movement operation of the drive shaft 140 are controlled by the controller 301. The connector unit 165 provided in the hub 160 is rotated in a state in which the connector unit 165 is connected to the external device 300. In conjunction with this rotation, the drive shaft 140 rotates. In accordance with the signals sent from the controller 301, the signal transceiver 145 transmits ultrasound and light into the body. The signals corresponding to the reflected waves and the reflected light received by the signal transceiver 145 are sent to the controller 301 via the drive shaft 140 and the external device 300. The controller 301 generates a tomographic image of the lumen in the living body in accordance with the signal sent from the signal transceiver 145, and displays the generated image on the monitor 302.

The image diagnosis catheter 100 according to the present embodiment is adapted to acquire a tomographic image of a biological lumen. The image diagnosis catheter 100 includes the sheath 110 having an elongated shape and provided with the lumen 110a, the rotatable drive shaft 140 disposed in the sheath lumen 110a of the sheath 110, the housing 146 disposed at a distal end portion of the drive shaft 140, and the optical transceiver 145b and the ultrasound transceiver 145a retaining in the housing 146. The optical transceiver 145b is provided with the reflecting surface (flat surface 145c) coated with a reflective coating. The reflective coating is configured to reflect light along an axial direction of the drive shaft. The center position of the optical transceiver 145b is disposed at a position apart from, or spaced from, the central position of the drive shaft 140 on a cross section orthogonal to the axial direction of the drive shaft 140. The housing 146 includes the side wall portion 146d disposed so as to cover at least the reflecting surface (flat surface 145c) of the optical transceiver 145b.

In the image diagnosis catheter 100 described above, the side wall portion 146d, which covers the reflecting surface (flat surface 145c), can inhibit or prevent the reflective coating from being separated by the flow of a priming liquid filled in the sheath 110 at the time of rotation. Therefore, an accurate tomographic image may be acquired even when the center position of the optical transceiver 145b is disposed at a position spaced from the central position (central axis) of the drive shaft 140 on a cross section orthogonal to the axial direction of the drive shaft 140.

Further, the optical transceiver 145b has a spherical surface 145d and the flat surface 145c disposed radially inward of the spherical surface 145d. The reflective coating is provided on the flat surface 145c. The side wall portion 146d covers the flat surface 145c (from the sides) and exposes the spherical surface 145d. Therefore, the flat surface 145c as a reflection surface is covered with or shielded by the side wall portion 146d, which can inhibit or prevent separation of the reflective coating, and the spherical surface serving as the light emitting surface is exposed, which can prevent the side wall portion 146d from obstructing the propagation of light.

The side wall portion 146d is formed integrally in one piece with the housing 146. Therefore, the number of components of the image diagnosis catheter 100 can be reduced compared to a case where the side wall portion 146d and the housing 146 are formed separately.

Although the image diagnosis catheter according to the present invention has been described thus far through the embodiment and the modification, the present invention is not limited to the configuration described in the embodiment and the modification, and may be modified as needed based on the description of claims.

For example, in the description of the above-described embodiment, an image diagnosis catheter according to the present invention is applied to the image diagnosis catheter having a function of intravascular ultrasound diagnosis (IVUS) technique and optical coherence tomography (OCT) technique. However, the image diagnosis catheter according to the present invention is not particularly limited unless it is an image diagnosis catheter using ultrasound and light as an inspection wave. For example, the image diagnosis catheter according to the present invention may be applied to an image diagnosis catheter provided with functions of an intravascular ultrasound diagnosis (IVUS) technique and an optical frequency domain imaging (OFDI) technique.

For example, in the description of the above-described embodiment, an ultrasound transmitted from the ultrasound transceiver and light transmitted from the optical transceiver intersect each other. For example, however, the direction of transmission of the ultrasound transmitted from the ultrasound transceiver, and the direction of transmission of the light transmitted from the optical transceiver may be parallel to each other. When the ultrasound and the light are parallel, the ultrasound and the light are spaced apart at a constant distance along the axial direction of the drive shaft. Therefore, for example, when a plurality of tomographic images are acquired using ultrasound and light as inspection waves with the pull-back operation, a tomographic image acquired by using the ultrasound as an inspection wave and a tomographic image acquired by using the light as an inspection wave acquired at the same position in the biological lumen may be extracted from a plurality of tomographic images considering that the ultrasound and light are apart from each other at a fixed distance.

For example, in the description of the above-described embodiment, an electrical signal cable (signal line) is comprised of two cables. However, the electrical signal cable may include, for example, a coaxial cable (one cable). The electrical signal cable may also be a twisted pair cable, in which two cables are wound around the optical fiber.

The detailed description above describes embodiments of an image diagnosis catheter representing an example of the inventive image diagnosis catheter disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An image diagnosis catheter for acquiring a tomographic image of a biological lumen, the image diagnosis catheter comprising:
   an elongated sheath that includes a lumen;
   a rotatable elongated member disposed in the lumen of the sheath;
   a housing disposed at a distal end portion of the elongated member, the housing having a longitudinal extent and including opposite sides each extending along the longitudinal extent of the housing;
an optical transceiver positioned in the housing;
the optical transceiver including a reflecting surface provided with a reflective coating that reflects light propagating in an axial direction of the elongated member; and
the housing including two side wall portions extending upwardly as seen from each of the sides of the housing, the reflecting surface of the optical transceiver being disposed between the two side wall portions at a position such that the two side wall portions extend above the reflecting surface of the optical transceiver as seen from each of the sides of the housing so that the reflecting surface of the optical transceiver is covered by the two side wall portions of the housing as seen from each of the sides of the housing.

2. The image diagnosis catheter according to claim 1, wherein
the optical transceiver includes a spherical surface and a flat surface located radially inward of the spherical surface,
the reflective coat is applied on the flat surface, and
the two side wall portions are disposed so that the flat surface is positioned between the two side wall portions and so that the spherical surface is exposed.

3. The image diagnosis catheter according to claim 2, wherein the flat surface is spaced from an axial center of the elongated member as seen in a cross section orthogonal to an axial direction of the elongated member.

4. The image diagnosis catheter according to claim 1, wherein the two side wall portions are integrally formed in one piece with the housing.

5. The image diagnosis catheter according to claim 1, further comprising: an ultrasound transceiver positioned in the housing.

6. The image diagnosis catheter according to claim 1, further comprising an ultrasound transceiver positioned in the housing at a position spaced from and distal of the optical transceiver.

7. An image diagnosis catheter for acquiring a tomographic image of a biological lumen, the image diagnosis catheter comprising:
an elongated sheath including a lumen;
a rotatable elongated member disposed in the lumen of the sheath;
a longitudinally extending housing disposed at a distal end portion of the elongated member, the housing including an interior surrounded by an outer wall of the housing;
an ultrasound transceiver positioned in the interior at a first longitudinally extending portion of the housing;
an optical transceiver positioned in the interior at a second longitudinally extending portion of the housing;
the housing including an opening as seen in a cross section orthogonal to an axial direction of the elongated member, the opening passing through the wall of the housing so that the opening communicates the interior of the housing with exterior of the housing, and the opening being larger in the first longitudinally extending portion of the housing in which the ultrasound transceiver is positioned than in the second longitudinally extending portion of the housing in which the optical transceiver is positioned, the opening being larger in the first longitudinally extending portion of the housing than in the second longitudinally extending portion of the housing as seen from a position facing the ultrasound transceiver and the optical transceiver.

8. The image diagnosis catheter according to claim 7, wherein the opening portion around the optical transceiver is bounded by circumferentially spaced apart side wall portions of the wall of the housing, the optical transceiver including a flat surface positioned between the two side wall portions.

9. The image diagnosis catheter according to claim 7, wherein the opening portion around the optical transceiver is bounded by circumferentially spaced apart side wall portions of the wall of the housing, the optical transceiver including a spherical surface facing radially outwardly and a flat surface facing radially inwardly further comprising a reflective coat on the flat surface of the optical transceiver, and the flat surface is positioned between the two side wall portions and the spherical surface is exposed.

10. The image diagnosis catheter according to claim 9, wherein the flat surface is spaced from an axial center of the elongated member as seen in the cross section orthogonal to an axial direction of the elongated member.

11. The image diagnosis catheter according to claim 9, wherein the two side wall portions are integrally formed in one piece with the housing.

12. The image diagnosis catheter according to claim 7, wherein the ultrasound transceiver is electrically connected to two electric signal cables, and the optical transceiver is connected to an optical fiber, the two electric signal cables being held in a first hole part in a positioning member and the optical fiber being held in a second hole part in the positioning member, a central axis of the optical fiber being spaced from a plane passing through a central axis of each of the two electric signal cables.

13. The image diagnosis catheter according to claim 7, wherein the ultrasound transceiver is spaced from and distal of the optical transceiver.

14. An image diagnosis catheter for acquiring a tomographic image of a biological lumen in a living body, the image diagnosis catheter comprising:
an elongated sheath that includes a lumen that receives priming fluid during operation of the image diagnosis catheter;
a rotatable driving shaft disposed in the lumen of the sheath and rotatable about a rotational axis;
a housing disposed at a distal end portion of the rotatable driving shaft, the housing having a longitudinal extent and including opposite sides each extending along the longitudinal extent of the housing;
an optical transceiver positioned in the housing and connected to an optical fiber, the optical transceiver including an optical element comprised of a radially outwardly facing spherical surface and a radially inwardly facing reflecting surface provided with a reflective coating so that light propagating from the optical fiber is reflected on the reflecting surface, is concentrated on the spherical surface and is then transmitted into the lumen in the living body;
the optical fiber possessing a central axis that is radially outwardly spaced from the rotational axis of the driving shaft, and a center of the optical transceiver being radially outwardly spaced from the rotational axis of the driving shaft; and
the housing including an opening that communicates the interior of the housing with exterior of the housing, the housing including two circumferentially spaced-apart side wall portions each located on a respective one of the sides of the housing, each side wall portion possessing an upper edge that borders a portion of the opening, the reflecting surface of the optical transceiver being positioned between the two side wall portions and being located below the upper edge of each of the side wall portions as seen from each of the sides of the housing so that the spaced-apart side wall portions of the housing cover the reflective surface coated with the reflective coating to inhibit separation of the reflective coating on the reflective surface due to the priming liquid during rotation of the driving shaft.

15. The image diagnosis catheter according to claim 14, wherein the spherical surface is exposed between the two side wall portions.

16. The image diagnosis catheter according to claim 14, wherein the reflective surface is a flat surface spaced from the rotational axis of the driving shaft.

17. The image diagnosis catheter according to claim 14, further comprising an ultrasound transceiver positioned in the housing.

18. The image diagnosis catheter according to claim 17, wherein the ultrasound transceiver is electrically connected to two electric signal cables that are held in a first hole part in a positioning member, the optical fiber being held in a second hole part in the positioning member, the positioning member being fixed inside the housing.

19. The image diagnosis catheter according to claim 18, wherein the central axis of the optical fiber being spaced from a plane passing through a central axis of each of the two electric signal cables.

20. The image diagnosis catheter according to claim 18, further comprising a depression in an outer peripheral surface of the positioning member to adjustably position the positioning member.

21. The image diagnosis catheter according to claim 20, wherein the housing includes a wall surrounding an interior in which is positioned the optical transceiver, the wall being provided with a notch that is aligned with the depression so that the depression is accessible from exterior of the housing.

22. The image diagnosis catheter according to claim 14, further comprising an ultrasound transceiver positioned in the housing at a position spaced from and distal of the optical transceiver.

* * * * *